United States Patent [19]

Montgomery

[11] Patent Number: 5,072,624
[45] Date of Patent: Dec. 17, 1991

[54] AUTOMATIC CONVEYOR TRANSITION SAMPLER

[75] Inventor: Jim R. Montgomery, Portland, Oreg.

[73] Assignee: Beloit Corporation, Beloit, Wis.

[21] Appl. No.: 570,675

[22] Filed: Aug. 22, 1990

[51] Int. Cl.[5] .......................... G01N 1/20; G01N 1/18
[52] U.S. Cl. .................. 73/863.91; 73/863.41; 73/863.52; 73/864.31
[58] Field of Search .......... 73/863.91, 863.92, 864.31, 73/864.32, 863.52, 863.53, 863.41

[56] References Cited

U.S. PATENT DOCUMENTS

| | | | |
|---|---|---|---|
| 280,994 | 7/1883 | Andrus | 73/863.41 |
| 2,498,601 | 2/1950 | Bylin et al. | 73/863.41 |
| 3,158,030 | 11/1964 | Cross | 73/864.31 |
| 3,853,009 | 12/1974 | Sutherland | 73/864.32 |
| 4,177,624 | 12/1979 | Kelpin | 175/58 X |
| 4,766,964 | 8/1988 | Hirota et al. | 73/433 X |

FOREIGN PATENT DOCUMENTS

| | | | |
|---|---|---|---|
| 674528 | 11/1963 | Canada | 73/863.52 |
| 676988 | 12/1963 | Canada | 73/863.53 |
| 234492 | 4/1986 | German Democratic Rep. | 73/864.32 |
| 5897 | 4/1964 | Japan | 73/863.53 |
| 423845 | 4/1974 | U.S.S.R. | 73/863.53 |
| 2077702 | 12/1981 | United Kingdom | 73/863.92 |

Primary Examiner—Tom Noland
Attorney, Agent, or Firm—Dirk J. Veneman; Raymond W. Campbell

[57] ABSTRACT

A sampler is disclosed for a flow of particulate material on a conveyor system which has at least one transfer point from a first conveyor to a second conveyor. The sampler has a sample bucket with a hinged bottom and a traveling rig which mounts the sample bucket to a fixed linear track spaced from the second conveyor. An electric motor drives a gear which engages with the track to move the traveling rig and bucket along the track from a first position over a sample collector to a second position aligned with the material flow from the first conveyor. The collector has two conduits. The first conduit leads to a sample repository and the second conduit leads to a conveyor for returning samples material to the material flow. An actuator-linkage assembly acts to move the sample bucket which is aligned with the material flow from a raised position where the bucket does not intercept the flow to a lowered position where substantially all the flow of material from the first conveyor is intercepted by the bucket. The assembly acts to retract the bucket from the lower, flow intercepting, position after a selected time. The rig then returns the bucket with the intercepted material to the first position over the splitter. An actuator on the bucket works a hinged bottom door to empty the sampled material from the bucket into the splitter, to permit a proportional fraction of the samples material to be collected.

6 Claims, 4 Drawing Sheets

AUTOMATIC CONVEYOR TRANSITION SAMPLER

FIELD OF THE INVENTION

The present invention relates to devices for sampling materials carried on conveyor belts in general and to devices for sampling materials at the junction or transition points of multiple conveyor belts in particular.

BACKGROUND OF THE INVENTION

In many processes involving conveyed particulate material it is desirable to periodically sample the material carried on the conveyor belts for anaylsis and control of the process. Sampling at the junction points between a main conveyor belt and a feeder belt can be cumbersome and samples retrieved may be inaccurate due to difficulties of sampling a proper cross section of the flow. Samplers which take material from the main belt must be exactly positioned in order to deal with the problems of stratification in which fines of the material traveling on the belt filter to the bottom. A sampler which does not take account of the fines will produce an inaccurate sample. Hand sampling may obtain an accurate cross section, but because the sampling process is not repeatable numerous variations in the sample introduced by human error result in unreliable data. Furthermore, it is difficult to obtain a sample which is large enough to accurately reflect the flow contents and yet which is small enough to be conveniently analyzed and stored.

What is needed is an apparatus which can automatically and consistently sample one or more transition points on a conveyor belt system and which can retrieve a large cross sectional sample across the full width of the belt and the entire depth of the flow material, and which can reliably reduce the size of the sample for sample classification purposes.

BRIEF DESCRIPTION OF THE INVENTION

The automatic conveyor sampler for a flow of Particulate material on a conveyor system which has at least one transfer point from a first conveyor to a second conveyor of this invention has a sample bucket with a hinged bottom and a traveling rig which mounts the sample bucket to a fixed linear track spaced from the second conveyor. The sampler has means for moving the traveling rig and bucket along the track from a first position over a sample collector to a second position aligned with the material flow from the first conveyor and for returning the rig and bucket to the collector afte a sample has been taken. The collector has two conduits. The first conduit leads to a sample repository and the second conduit leads to a conveyor for returning sampled material to the material flow. A means is provided for moving the sample bucket which is aligned with the material flow from a raised position where the bucket does not intercept the flow to a lowered position where substantially all the flow of material from the first conveyor is intercepted by the bucket and for retracting the bucket from the lower, flow intercepting, position after a selected time. Means is further provided for emptying the sampled material from the bucket into the collector. A splitter gate is adjustably positioned between the conduits to permit a proportional fraction of the sampled material to be collected.

It is an object of this invention to provide an automatic sampler which will take consistant and repeatable samples of the flow material at the transition point between two conveyor belts.

It is also an object of the present invention to provide a automatic sampler which will take a sample across the full width of a belt and the entire depth of the flow material.

It is another object of the present invention to provide a sampler which will accurately reduce in size a sample.

It is a further object of the present invention to provide a sampler which will automatically sample the material flow at two or more transition points.

Further objects, features, and advantages of the invention will be apparent from the following detailed description when taken in conjunction with the accompanying drawings.

DESCRIPTION OF THE PREFERRED EMBODIMENT

Figure 1:
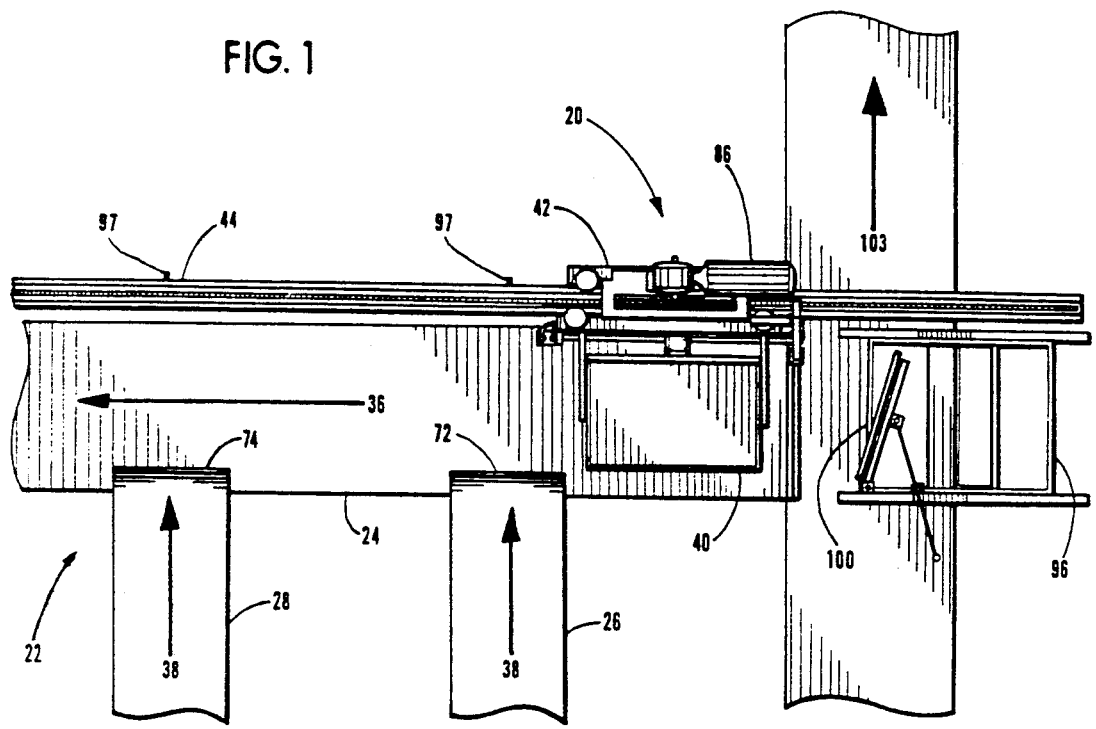
FIG. 1 is a schematic view of the automatic conveyor sampler of this invention shown in conjunction with a system of conveyor belts.

Referring now to FIGS. 1-6, wherein like numbers refer to similar parts, a conveyor sampler 20 is shown in FIG. 1 in relation to a conventional system of conveyor belts 22, having a main belt 24, and first and second feed belts 26, 28. A particulate material 34, such as wood chips, is carried on the belts 24, 26, 28 with the direction of material flow on the main belt 24 shown by the arrow 36 and the direction of flow on the feed belts 26, 28 shown by the arrows 38.

Figure 2:
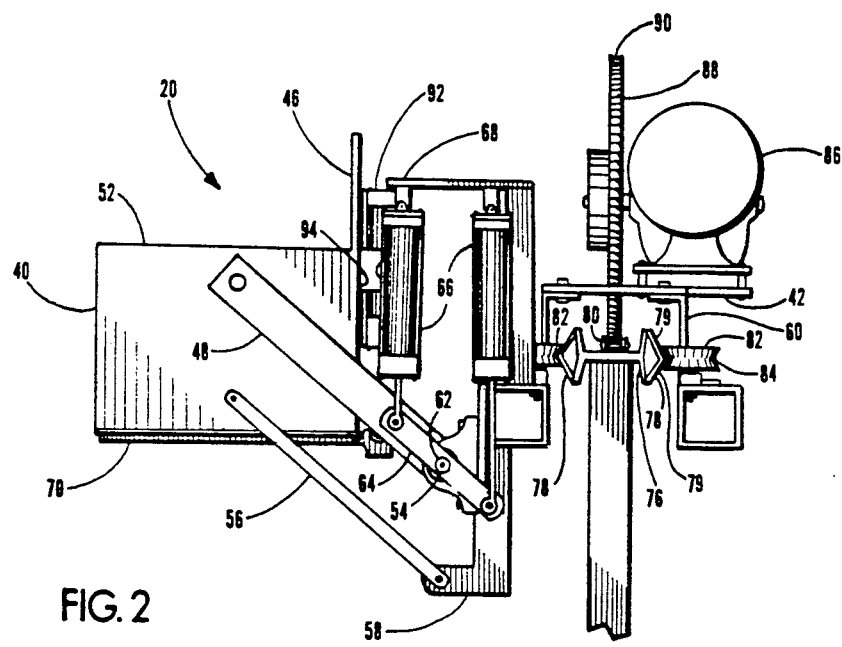
FIG. 2 is a right side elevational view of the conveyor sampler of this invention.

As best seen in FIG. 2, the conveyor sampler 20 has a sample bucket 40 which is mounted on a traveling rig 42 in such a way that it may be moved between a raised and a lowered position. The traveling rig runs on a linear track 44 which is aligned with and spaced from the main belt 24.

The sample bucket 40 is a wooden or preferably welded metal plate box which is wide enough to receive the full width of the material 34 flow from a feed belt and has a sufficiently large volume to accommodate a sample of the desired size. A back stop 46 extends at the rear of the box and serves to redirect material into the bucket 40.

Means for moving the sample bucket between a raised Position which does not interfere with the flow and a lowered flow-intercepting position is provided by an actuator driven system of mechanical parallel linkages. Two driven members 48 are rotatably attached to the sides 52 of the sample bucket 40 at one end and are fixedly attached at the other end to an elevator rod 54.

Figure 3:
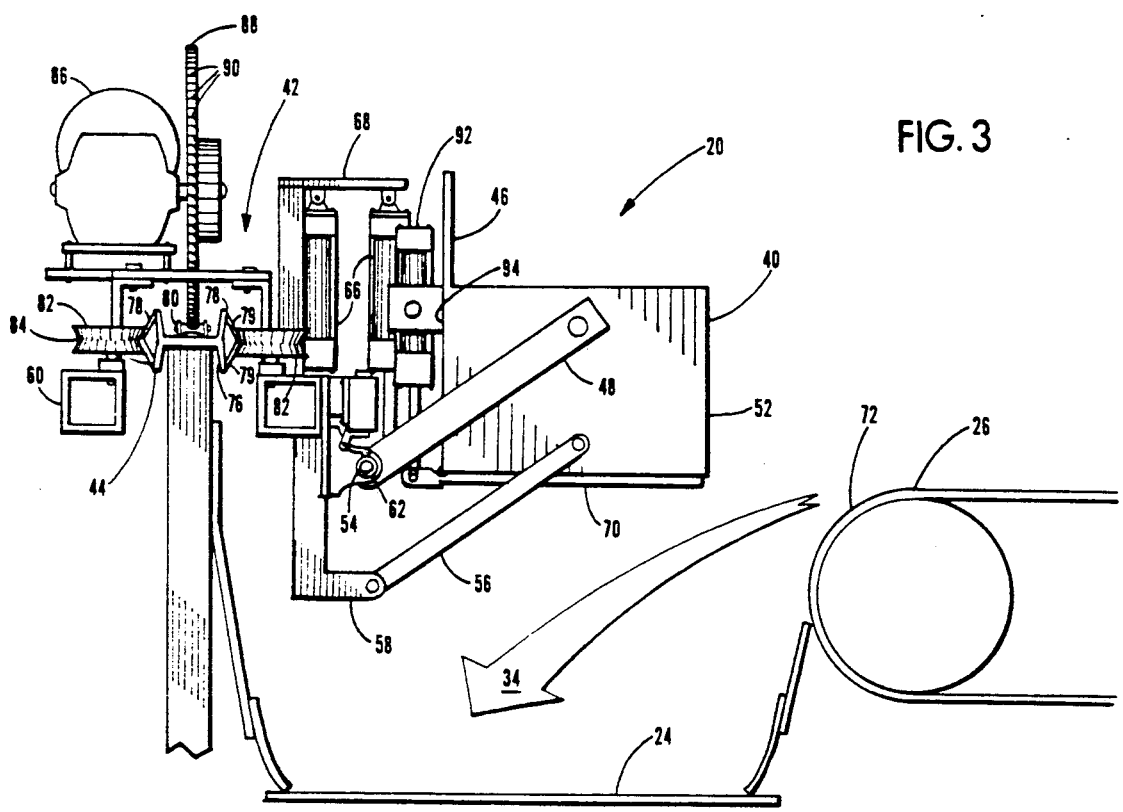
FIG. 3 is a left side elevational view of the conveyor sampler of FIG. 2 in a raised position aligned with a material flow.
Figure 4:
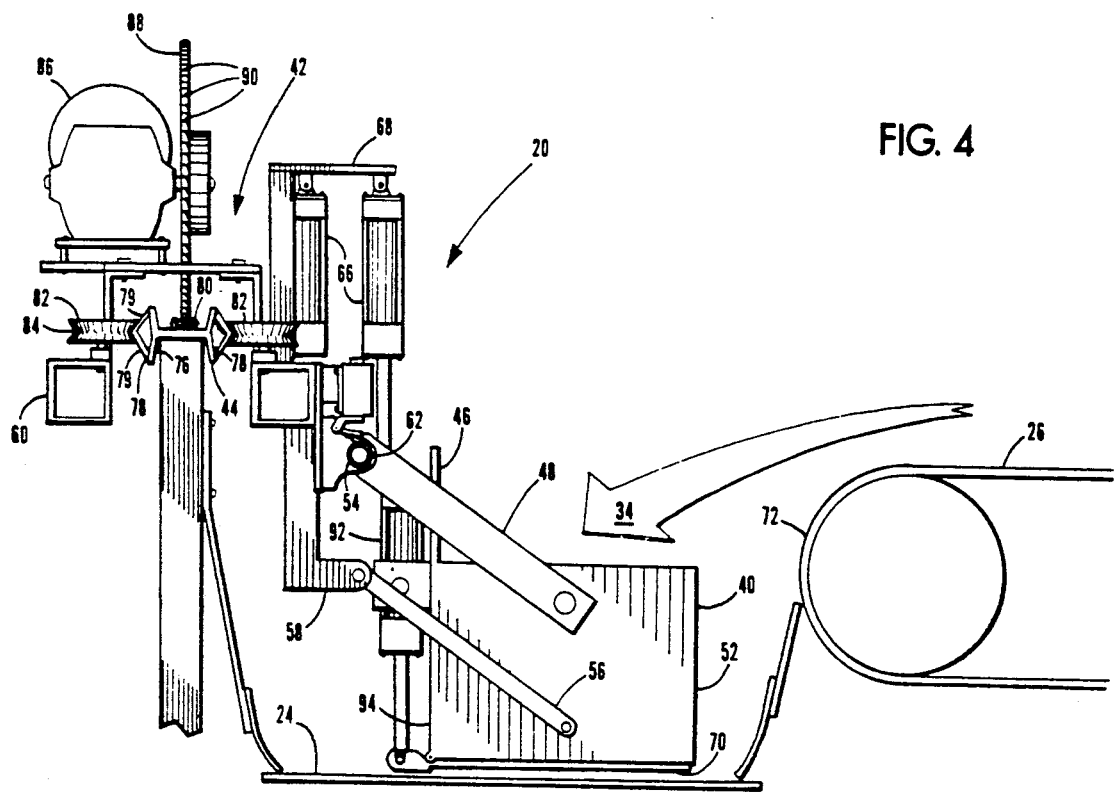
FIG. 4 is a side elevational view of the apparatus of FIG. 3 in a lowered position to sample the material flow.

Positioning members 56 are rotatably connected to the sides 52 of the sample bucket 40 directly below the driven members 48 and are rotatably connected to projections 58 from the frame 60 of the traveling rig 42. The actuators comprise conventional hydraulic or preferably pneumatic cylinder-piston assemblies. The actuators may be single or double acting. The elevator rod 54 is journaled into bearings 62 attached to the traveling rig 42 frame 60. An elevator member 64 is rigidly mounted at its center to the elevator rod 54 and extends perpendicularly on either side of the elevator rod 54. Elevator actuators 66 are attached to either end of the elevator member 64 and are rotatably connected to the outwardly extending cylinder member 68 which is rigidly connected to the frame 60 of the traveling rig 42. For clarity in the figures, pneumatic hoses and electrical cables have not been shown. The hoses and cables must be long enough to reach the furthest extension of the traveling rig 42 and may be coiled and carried on rings on a wire running alongside the main belt in a conventional manner. By alternately extending and retracting the elevator actuators 66, the bucket 40 may be moved from a raised position as shown in FIG. 3 to a lowered position as shown in FIG. 4. The connections of the driven members 48 and the positioning members 56 insure that the hinged bottom door 70 of the sample bucket 40 remains parallel to the main belt 24.

The traveling rig 42 supports the sample bucket 40 on the linear track 44, and moves the bucket along the track 44 in order to selectively take samples at the transition points 72, 74 between the main belt 24 and the first and second feed belts 26, 28 respectively. The track 44 is composed of a central I-beam 76 with angled brackets 78 welded to either side to form sides with two angled faces 79. A length of chain 80 is stretched down the center of the I-beam 76 and is connected to the I-beam 76. Four rotatable track guides 82 are mounted on the frame 60 of the traveling rig 42. Each track guide 82 has two joined frustoconical segments which form a V-shaped circumferential groove 84 around the track guide 82. The angle brackets 78 fit within the grooves 84 of the track guides 82. The traveling rig 42 and the bucket 40 are thus supported on the track 44 by the track guides 82. Means for transporting the traveling rig 42 and bucket 40 along the track 44 is provided by a motor driven gear which engages a chain 80 on the track 44. An electric gear reduction motor 86 is mounted on the frame 60 and turns a drive gear 88. The drive gear has teeth 90 which engage with the chain 80 such that when the drive gear is turned the traveling rig 42 will move along the track 44.

A bottom door actuator 92, which is preferably a double acting pneumatic cylinder-piston assembly, is connected to the rear 94 of the sample bucket 40 behind the backstop 46 and is connected to the bottom door 70 of the bucket 40 such that by extending and retracting the actuator 92, the bottom door 70 may be opened and closed.

The travel of the traveling rig 42, the elevation of the bucket 40 and the position of the bottom door 70 are controlled by a controller (not shown) which may be a microprocessor or a conventional mechanical, analog electrical or pneumatic control system. The preferred embodiment employs limit switches 97 shown schematically in FIG. 1 positioned along the track 44 spaced from the transition points 72, 74 to cause the controller to halt the traveling rig 42 at a location for taking a sample.

When a sample is desired, or at preprogrammed intervals, the traveling rig 42 moves out along the track 44 with the bucket 40 in a raised position. In its raised Position the traveling rig 42 may be carried past any number of transition points without interfering with the flow of material onto the main belt 24 and without collecting any material from the feed belts passed by. In FIGS. 3 and 4 the flow of Particulate material 34 is indicated by schematic oversized arrows. The traveling rig 42 is halted on the track 44 in a position aligned with the flow of particulate material 34 at a transition point, as shown in FIG. 3. When the bucket 40 is raised the material flow is uninterrupted, allowing all the particulate material 34 carried on the feed belt to transfer to the main belt 24. Once aligned with the transition point the controller actuates the elevator actuators 66 to displace the ends of the elevator member 64 to cause a rotation of the elevator rod 54 moving the bucket 40 into a lower position which intercepts the flow of particulate material 34 from the feed belt 26, as shown in FIG. 4. The bucket 40 is maintained in the lowered position for a preset length of time. While lowered, the bucket 40 intercepts the entire flow of material from the feed belt 26. The backstop 46 serves to redirect into the bucket material which would otherwise overshoot the bucket 40. The size of the sample 98 collected will depend upon the time the bucket is retained in a lowered position and the flow rate of material 34.

Figure 5:
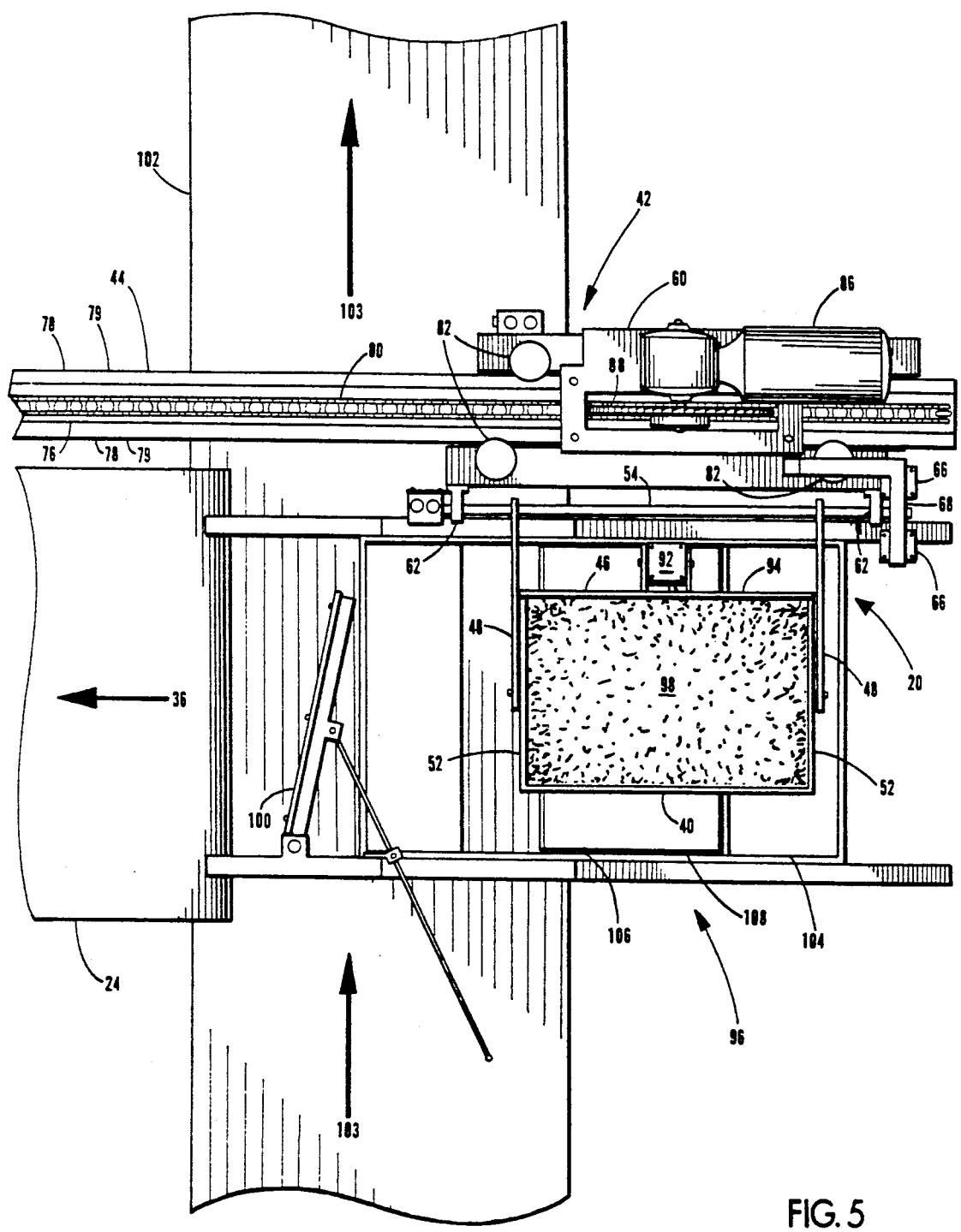
FIG. 5 is a top view of the conveyor sampling apparatus of this invention fully loaded with a sample and in position over a sample splitter.
Figure 6:
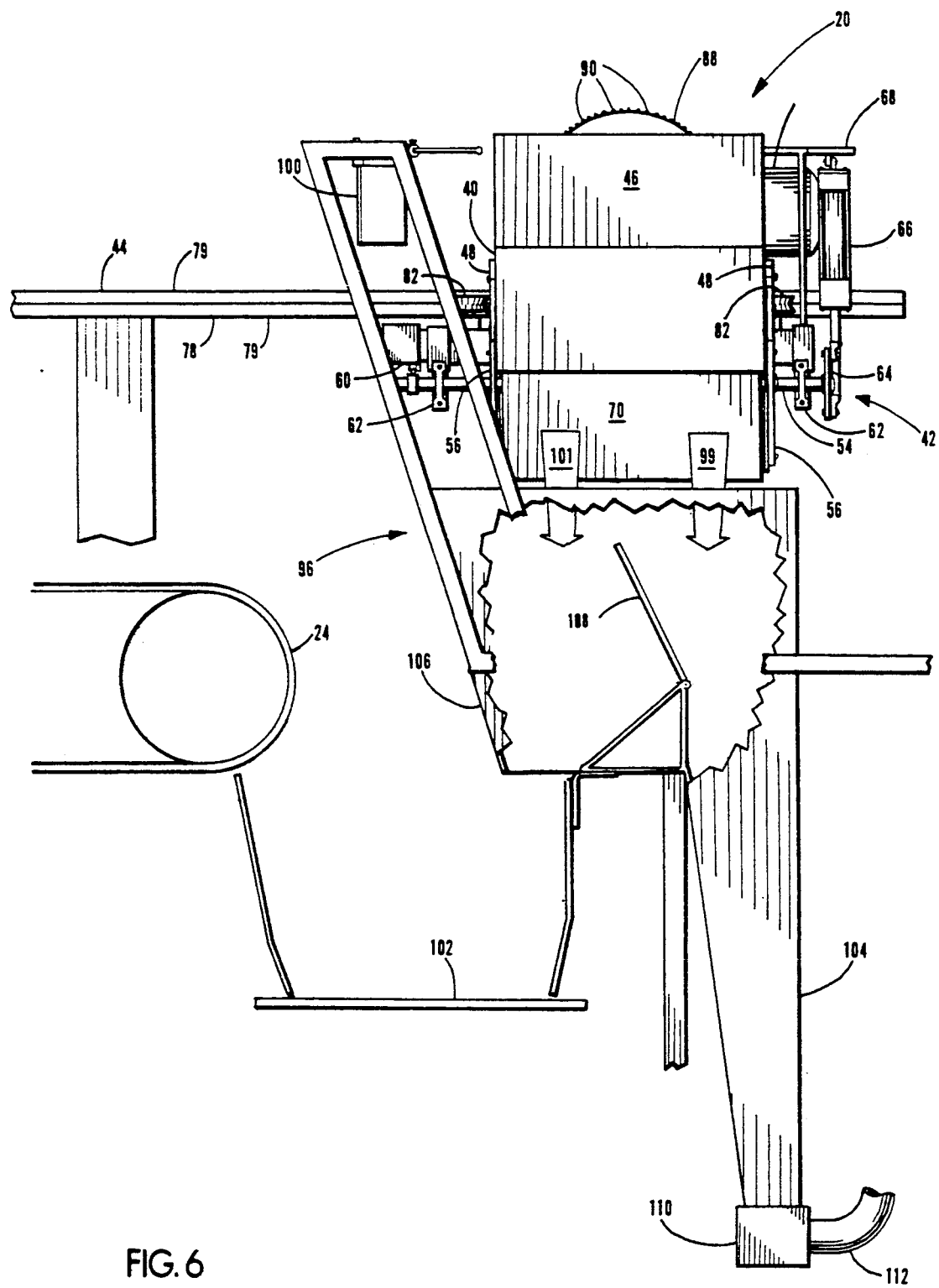
FIG. 6 is a front elevational view of the conveyor sampler of FIG. 5 unloading a sample into the splitter with a portion broken away in section.

After a predetermined time in the lowered position the elevator cylinders 66 are actuated to return the bucket 40 to a raised position, and the electric motor 86 is activated to return the traveling rig 42 to its original position overlying the sample collector or splitter 96, as shown in FIG. 5.

In returning to the splitter 96, the loaded bucket 40 passes under a wiper blade 100 affixed to the splitter 96. The wiper blade 100 levels the sample 98 within the bucket 40 and removes sampled material in excess of the bucket capacity. The removed material preferably falls on a return conveyor 102 which returns the material 34 to the main belt 24.

The splitter 96 is divided into two conduits, a sample conduit 104 and a return conduit 106. An adjustable splitter gate 108 is located within the splitter 96 and determines the proportion of the sample 98 emptied into the splitter 96 which will go to each conduit 104, 106. The splitter gate 108 may be rotated to enlarge the opening to the sample conduit 104 or to the return conduit 106. By adjusting the relative sizes of the openings to the sample and return conduits the size of the sampled portion 99 may be adjusted while retaining a portion 99 that is representative of the entire sample 98. If the opening to the sample conduit 104 is enlarged, the opening to the return conduit 106 is reduced and the amount of sample flowing through each conduit 104, 106 will be likewise affected.

Means for discharging the collected sample 98 is provided by the bottom door 70 and the bottom door actuator 92. When the traveling rig 42 comes to rest over the splitter 96, as shown in FIG. 5, the bottom door actuator 92 is activated to lower the bottom door 70, allowing the entire sample 98 to flow from the bucket 40 into the splitter 96. The sample 98 is split by the splitter gate 108 into the sampled portion 99 and a returned portion 101 shown by large arrows in FIG. 6. The sampled portion 99 flows through the sample conduit 104 and is directed to a vibrating tray 110. The vibrating tray 110 assists in the dislodgement of any particles which may adhere to the walls of sample conduit 104. The tray 110 feeds a pneumatic conveying system 112 which transports the sample to a desired location or repository. This location may be a lab, a collection site, a classifier or other end use of the sample.

The returned portion 101 of the sample 98 flows through the return conduit 106 and is ducted to the return conveyor 102 which returns it to the main belt 24.

By adjusting the splitter gate 108 samples of any desired size may be obtained which accurately and proportionately reflect the contents of the sampled flow.

After collecting and transporting to the splitter 96 the first sample 98, the traveling rig is free to return to a second transition point to take a new sample or to return to the first transition point to take an additional sample.

It should be noted that the conveyor sampler 20 may be adapted to suit main belts with any number of feed belts with appropriate programming, track and limit switches. A conveyor sampler for only one feed belt is also possible. Although hydraulic, or preferably, pneumatic cylinders may be used to raise and lower the sample bucket and to open and close the bucket bottom door, any conventional mechanical linkages may be substituted to obtain the same results. Furthermore, while an assembly of two double acting actuators is shown for raising and lowering the sample bucket a pair of single acting actuators or a single double acting cylinder may perform the same function with suitable linkages.

It is understood that the invention is not confined to the particular construction and arrangement of parts herein illustrated and described, but embraces such modified forms thereof as come within the scope of the following claims.

I claim:

1. A sampler for a flow of particulate material on a conveyor system having at least one transfer point from a first to a second conveyor, comprising:
    a sample bucket having sides and a bottom for retaining sampled material;
    a fixed linear track spaced from the second conveyor;
    a traveling rig which mounts the sample bucket to the track and which permits the bucket to move along the track;
    a sample collector spaced from the second conveyor;
    means for transporting the traveling rig and bucket along the track from a first position over the collector to a second position aligned with the material flow from the first conveyor and for returning a collected sample to the collector;
    means for moving the sample bucket when in the second position aligned with the material flow from the first conveyor between a raised position where the bucket does not intercept the flow and a lowered position where substantially all the flow of material from the first conveyor is intercepted by the bucket, and for retracting the bucket from the lower, flow intercepting, position after a selected time; and
    bucket emptying means for discharging the sampled material from the bucket into the collector.

2. The sampler of claim 1 wherein the bucket bottom is hinged and the bucket emptying means comprises a means for lowering the bottom of the bucket to allow the sampled material to drop from the bucket into the sample collector.

3. The sampler of claim 1 wherein the sample collector comprises:
    a first conduit connecting with a sample repository and a second conduit not connected to the sample repository; and
    a splitter gate located between the first and second conduits and adjustably positioned beneath the sample bucket in the first position so as to direct a fraction of the sampled material emptied from the bucket into the first conduit so that a sample portion will be conveyed to the sample repository which is proportional to the entire sample.

4. The sampler of claim 3 further comprising a return conveyor beneath the second conduit of the sample collector which returns the fraction of sampled material not conveyed to the repository to the second conveyor.

5. The sampler of claim 1 wherein the means for moving the traveling rig along the track comprises a motor which drives a rotatable gear, and the fixed track comprises an I-beam with angle brackets connected to each side of the I-beam with a length of chain fixed to the center of the I-beam and the gear engages with the chain to move the traveling rig.

6. A sampler for a flow of particulate material on a conveyor system having at least one transfer point from a first to a second conveyor, comprising:
    a sample bucket having sides and a hinged bottom for retaining sampled material;
    a fixed linear track spaced from the second conveyor;
    a traveling rig which is connected by parallel linkages to the sample bucket and which is mounted to the track to permit the bucket to move along the track;
    a motor which drives a rotatable gear which engages with the track to move the traveling rig and bucket along the track from a first position to a second position aligned with the material flow from the first conveyor;
    an actuator between the rig and the linkage adapted to move the sample bucket when in the second position aligned with the material flow from the first conveyor between a raised position where the bucket does not intercept the flow and a lowered position where substantially all the flow of material from the first conveyor is intercepted by the bucket, wherein the actuator may retract the bucket from the lower, flow intercepting, position after a selected determinate time and return the bucket with the intercepted material to the first position over the collector;
    an actuator mounted between the bucket bottom and the bucket to permit the discharge of the sampled material from the bucket, by lowering the bucket bottom.

* * * * *

UNITED STATES PATENT AND TRADEMARK OFFICE
CERTIFICATE OF CORRECTION

PATENT NO. : 5,072,624

DATED : December 17, 1991

INVENTOR(S) : James R. Montgomery

It is certified that error appears in the above-identified patent and that said Letters Patent is hereby corrected as shown below:

On the title page, In the Abstract:

Lines 13 & 26: "samples" should read --sampled--.

Signed and Sealed this

Sixth Day of April, 1993

*Attest:*

STEPHEN G. KUNIN

*Attesting Officer*    Acting Commissioner of Patents and Trademarks